(12) United States Patent
Lawrence (10) Patent No.: US 9,259,143 B2
(45) Date of Patent: *Feb. 16, 2016

(54) ILLUMINATED DENTAL RETRACTOR

(71) Applicant: Kenneth H. Lawrence, Beachwood, OH (US)

(72) Inventor: Kenneth H. Lawrence, Beachwood, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/861,500

(22) Filed: Apr. 12, 2013

(65) Prior Publication Data

US 2013/0230823 A1  Sep. 5, 2013

Related U.S. Application Data

(63) Continuation of application No. 12/704,846, filed on Feb. 12, 2010, now Pat. No. 8,419,428.

(60) Provisional application No. 61/151,948, filed on Feb. 12, 2009.

(51) Int. Cl.
| | |
|---|---|
| *A61C 5/00* | (2006.01) |
| *A61C 3/00* | (2006.01) |
| *A61B 1/24* | (2006.01) |
| *A61B 1/247* | (2006.01) |
| *A61B 1/32* | (2006.01) |
| *A61B 1/06* | (2006.01) |

(52) U.S. Cl.
CPC .............. *A61B 1/24* (2013.01); *A61B 1/0676* (2013.01); *A61B 1/0684* (2013.01); *A61B 1/247* (2013.01); *A61B 1/32* (2013.01); *A61B 1/06* (2013.01)

(58) Field of Classification Search
CPC ............ A61B 1/06; A61B 1/24; A61B 1/247; A61B 1/32; A61B 1/0676; A61B 1/0684; A61B 1/006; A61C 1/088; A61C 5/114
USPC ............... 433/29, 140, 93; 600/238; 128/859; 466/29, 140, 93
See application file for complete search history.

(56) References Cited

U.S. PATENT DOCUMENTS

| | | | |
|---|---|---|---|
| 4,592,344 A | | 6/1986 | Scheer |
| 5,037,298 A | * | 8/1991 | Hickham .................... 433/93 |
| 5,711,665 A | | 1/1998 | Adam et al. |
| 6,719,447 B1 | | 4/2004 | Woodward et al. |
| 6,908,308 B2 | | 6/2005 | Hirsch et al. |
| 2004/0106082 A1 | * | 6/2004 | Rizoiu et al. .................. 433/29 |

(Continued)

FOREIGN PATENT DOCUMENTS

| | | |
|---|---|---|
| GB | 2 448 240 A | 10/2008 |
| JP | 04090753 A * | 3/1992 ............ A61C 19/00 |

(Continued)

OTHER PUBLICATIONS

Translation of the abstract JP404090753A, 1992.*

(Continued)

*Primary Examiner* — Heidi M Eide
(74) *Attorney, Agent, or Firm* — Richard M. Klein; Fay Sharpe LLP (57) ABSTRACT

A dental apparatus for retracting the cheeks and lips of a patient and illuminating the oral cavity of a patient is provided. The dental apparatus includes LEDs mounted on the cheek retractors. The apparatus allows a dentist to illuminate the interior of the oral cavity without needing additional equipment that hinders access to the oral cavity.

17 Claims, 5 Drawing Sheets

(56) References Cited

U.S. PATENT DOCUMENTS

| | | |
|---|---|---|
| 2005/0239017 A1 | 10/2005 | Lim |
| 2005/0239018 A1 | 10/2005 | Green et al. |
| 2006/0040230 A1 | 2/2006 | Blanding et al. |
| 2006/0069316 A1 | 3/2006 | Dorfman et al. |
| 2006/0154197 A1 | 7/2006 | Gargiulo |
| 2006/0155171 A1 | 7/2006 | Yang |
| 2006/0172252 A1* | 8/2006 | Suzuki ............................ 433/29 |
| 2007/0156028 A1 | 7/2007 | Van Lue et al. |
| 2008/0096165 A1 | 4/2008 | Virnicchi et al. |
| 2008/0113312 A1 | 5/2008 | Ortega |

FOREIGN PATENT DOCUMENTS

| | | |
|---|---|---|
| WO | WO 2006/008278 | 1/2006 |
| WO | WO 2006/026129 A1 | 3/2006 |
| WO | WO 2007/046585 A1 | 4/2007 |

OTHER PUBLICATIONS

International Search Report and Written Opinion, dated Apr. 14, 2010, in connection with International Appln. No. PCT/US2010/024033.

Extended European Search Report, dated Spe. 4, 2012, in connection with European Appln. No. 10741773.5.

\* cited by examiner

ILLUMINATED DENTAL RETRACTOR

This application is a continuation of U.S. patent application Ser. No. 12/704,846, filed Feb. 12, 2010, now U.S. Pat. No. 8,419,428, which claims priority from U.S. Provisional Patent Application Ser. No. 61/151,948, filed Feb. 12, 2009. The entirety of each application is hereby incorporated by reference herein.

BACKGROUND

The present disclosure relates to dental apparatuses for illuminating the oral cavity of a patient's mouth. The apparatuses include cheek retractors and light emitting diodes (LEDs) to provide substantially uniform illumination during use.

Illuminating the oral cavity during dental procedures is important for effective treatment. Dentists must be able to see, review, and access the inside of a patient's mouth clearly during dental examinations, checkups, cleanings, dental procedures, and oral surgery. However, access to the interior of the mouth is difficult, in part because the oral cavity is generally accessed through only one opening, the lips. All equipment must pass through the lips, but the dentist must remain able to see the interior of the mouth.

Exterior light sources are common. However, the common dental lamp has many drawbacks. The exterior light can be easily blocked by, for example, the dentist's head or hands, the equipment, or the patient's teeth, gums, lips, or tongue. All of these body parts can cause shadows that hinder the dentist's sight. The intensity of the light illumination diminishes as the distance between the light source and the patient increases. Also, external lights can cause discomfort in a patient's eyes. Finally, some portions of the oral cavity, such as the lingual side of the incisors, cannot be illuminated directly from outside the mouth without significant re-positioning and uncomfortable posture changes on the part of the both the patient and dentist.

Some devices place a light source between the dentist and the mouth, which removes shadows caused by the dentist. However, these devices can occupy desired space in the oral cavity or block the mouth itself, which can hinder the dentist's access to the interior of the mouth and/or significantly impair the dentist's range of motion and ability to effectively perform dental procedures.

It would be desirable to provide an interior light source for the oral cavity that reduces these problems.

BRIEF DESCRIPTION

Disclosed, in various embodiments, are dental apparatuses for retracting the cheeks and lips and illuminating the oral cavity of a patient. The apparatus has a light illumination system which uses light emitting diodes to illuminate the interior of the mouth. The dental apparatuses comprise two retractors, an arm connecting the retractors, and at least one LED. The at least one LED is attached to the dental apparatus such that the interior of a patient's mouth can be illuminated without an external light source.

Disclosed in some embodiments is a dental apparatus or system comprising two cheek retractors and a flexible arm that connects the two retractors. At least one of the retractors comprises a U-shaped trough; a ridge extending transversely from the trough and away from the arm; and one or more light-emitting diodes (LED) secured to the ridge. Alternatively, both retractors are as described.

In further embodiments, there is one LED attached to each retractor. In others, two, three, four, or more LEDs are attached to each retractor. The LEDs can be secured along a centerline of the ridge.

In specific embodiments, the ridge is offset towards a superior edge of the retractor to cover Stenson's duct. The ridge of the retractor extends from about 1 to about 1.5 inches in various embodiments. In some embodiments, the ridge extends about 1.25 inches. The U-shaped trough may have a depth of from about 0.25 to about 0.5 inches. The retractor may also have a power cord for powering the at least one LED, the power cord extending from an exterior side of the trough.

An angle exists between the U-shaped trough and the ridge. That angle is between about 40 and about 80° in several embodiments. That angle can also be between about 50 and about 70°. In some specific embodiments, the angle is about 60°.

The arm of the apparatus may include one or more mechanisms for securing or holding a hose or tube (e.g. suction or power supply cord), such as a hook. The apparatus may further comprise an external battery and control system that is adapted to independently power the LED on each retractor.

The LED may alternatively be embedded in the ridge. The resulting ridge may have a smooth inner surface, or a raised inner surface, depending on the depth to which the LED is embedded. The ridge may comprise a substantially transparent material through which the LED transmits light. In embodiments, the substantially transparent material has a transparency of at least 90 percent as measured by ASTM D1003.

Disclosed in other embodiments is a dental apparatus or system comprising two cheek retractors and a flexible arm that connects the two retractors. At least one retractor comprises a lip-oriented face; an oral cavity-oriented face; and at least one light-emitting diode located on the oral cavity-oriented face.

The lip-oriented face may include a U-shaped trough and the oral cavity-oriented face may be on a ridge extending transversely from the lip-oriented face and away from the arm.

Disclosed in still other embodiments is a dental apparatus comprising two cheek retractors; a flexible arm for connecting the two retractors; and an external control system. Each cheek retractor comprises a U-shaped trough, a ridge, at least one light-emitting diode (LED), a joint, and a power cord. The U-shaped trough has two ends and a nadir. The ridge is attached to an interior side of the trough, extends transversely from the trough, and is offset towards a superior side of the trough. The at least one LED is embedded in the ridge on an inner surface. The joint is used to connect the cheek retractor to the arm. The joint has a slot and extends from the nadir away from the two ends of the trough. The power cord extends from the exterior side of the trough and is used to power the at least one LED. The flexible arm has two ends, and each end has a tab that engages the slot on the joint to connect a cheek retractor to the arm. The external control system includes a battery for powering the LEDs on each retractor, and controls for turning the LEDs on and off.

In some embodiments, the power cords of the two cheek retractors are joined together to form a Y connection, integrally connecting the two retractors together. Put another way, the two retractors are integrally joined to each other through their power cords.

A method for illuminating the oral cavity is also disclosed. The method comprises placing a dental apparatus in a patient's mouth and turning on at least one LED. The dental apparatus comprises two retractors, an arm connecting the retractors, and at least one LED. Each retractor has a U-shaped trough and a ridge extending transversely from the trough and away from the arm. The at least one LED is attached to the ridge.

These and other non-limiting characteristics are more particularly described below.

BRIEF DESCRIPTION OF THE DRAWINGS

The following is a brief description of the drawings, which are presented for the purposes of illustrating the disclosure set forth herein and not for the purposes of limiting the same.

DETAILED DESCRIPTION

A more complete understanding of the apparatuses disclosed herein can be obtained by reference to the accompanying drawings. These figures are merely schematic representations based on convenience and the ease of demonstrating the present disclosure, and are, therefore, not intended to indicate relative size and dimensions of the apparatuses thereof and/or to define or limit the scope of the exemplary embodiments.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

The modifier "about" used in connection with a quantity is inclusive of the stated value and has the meaning dictated by the context (for example, it includes at least the degree of error associated with the measurement of the particular quantity). In addition, the value or range endpoints so modified should also be considered as being disclosed. For example, the range "about 2 to about 4" should also be considered as disclosing the range "2 to 4".

Referring to FIGS. 1-5, the dental apparatus 10 comprises two cheek expanders or retractors 20, 30. An arm 40 or crossbar is connected to the two retractors, and the retractors 20, 30 can be separated from the arm. The arm has two ends 46, 48. The arm is generally made of a flexible material (see FIG. 3) and is biased to separate the two retractors 20, 30 and increase the size of the mouth. Put another way, the arm should be able to "spring" between a flexed state and a relaxed state. In the relaxed state, the two ends 46, 48 are further apart than in the flexed state.

Figures 1, 2:
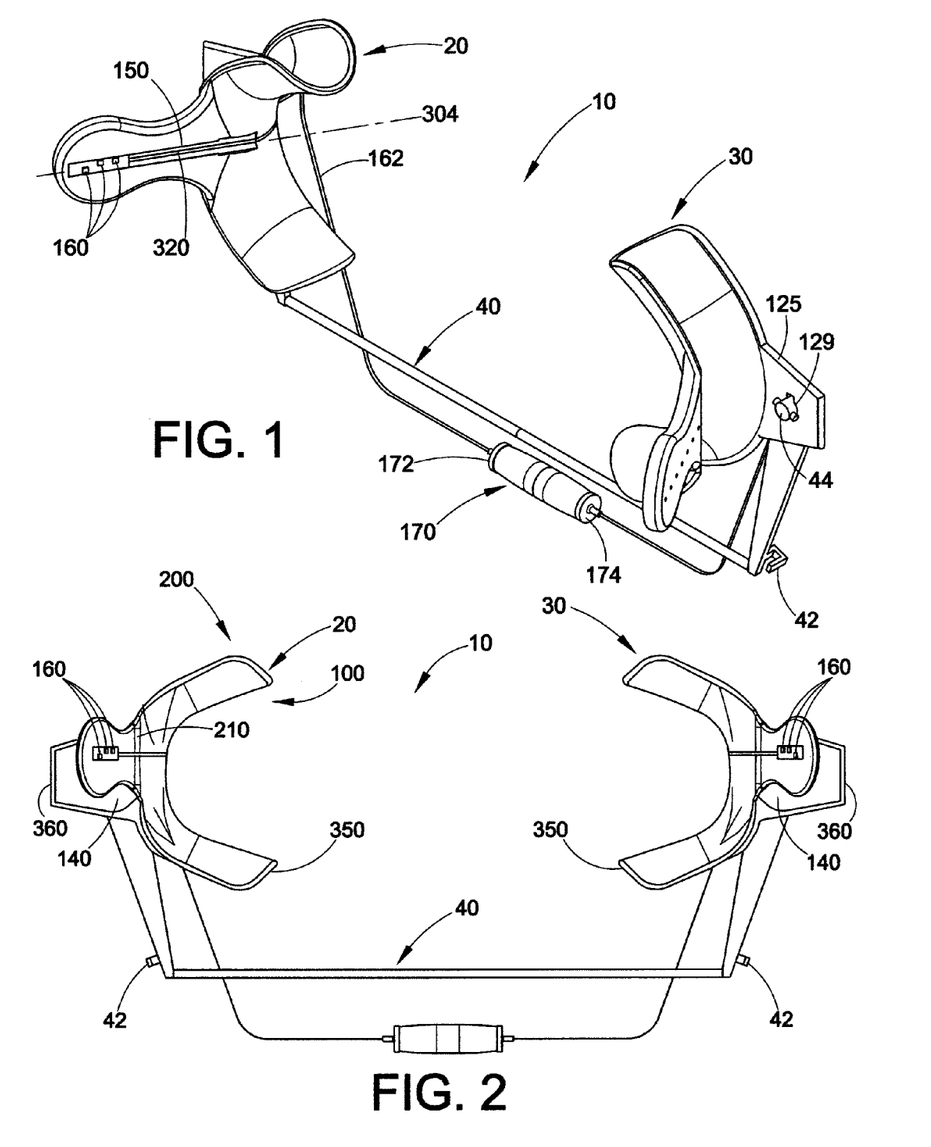
FIG. 1 is a perspective view of an exemplary dental apparatus.
FIG. 2 is a front view (i.e. from a patient's point of view) of an exemplary dental apparatus.

The arm 40 may have any shape generally suitable for holding a patient's mouth open without causing discomfort. The arm 40 includes one or more securing members 42 on either side, which can be used to hold a hose or tube being used for another purpose (e.g. suction or power supply cord).

Here, the securing member is depicted as a hook, but other mechanisms, such as grips or clamps, are also contemplated. The arm, in its fully biased, relaxed state, may have a length of about 8.2 inches between the two ends 46, 48. In use, the arm is located so that the arm itself does not block the dentist's access to the mouth or discomfort the patient, i.e. the arm hangs below the retractors 20, 30.

Figure 3:
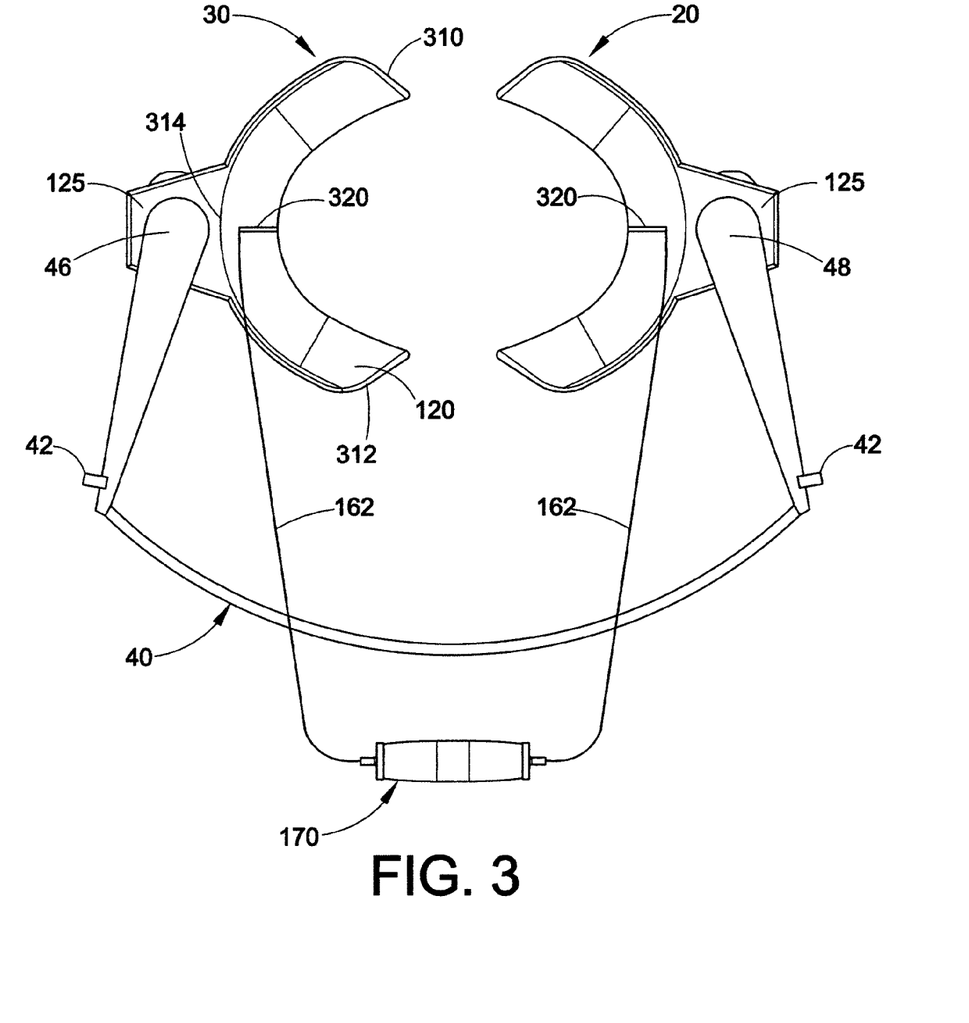
FIG. 3 is a rear view (i.e. from a dentist's point of view) of an exemplary dental apparatus.
Figures 4, 5:
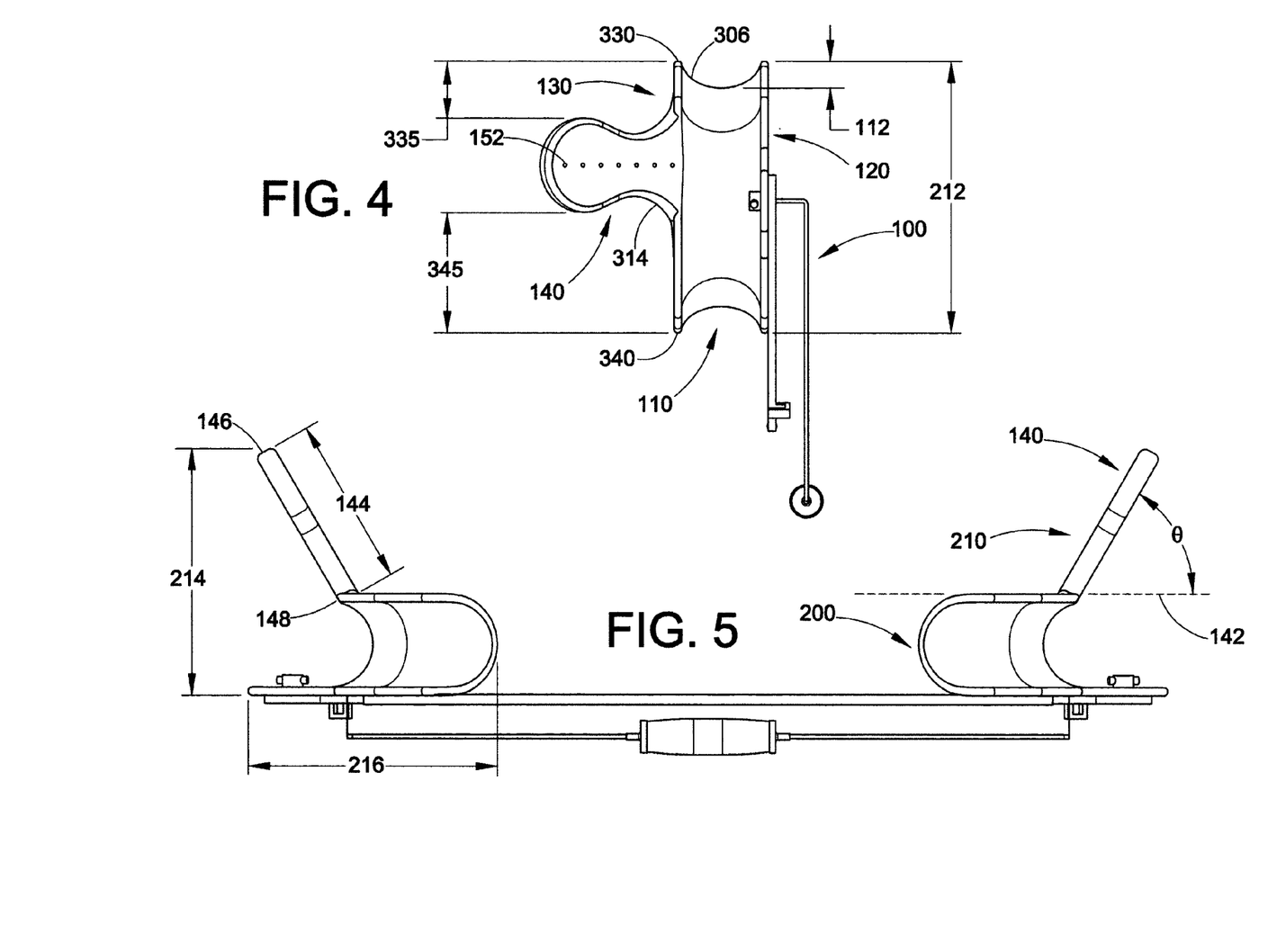
FIG. 4 is a side view of an exemplary dental apparatus.
FIG. 5 is a top view of an exemplary dental apparatus.

Referring to FIG. 3 and FIG. 4, the cheek retractor 100 includes a U-shaped trough 110 that engages the lips and cheek. The U-shaped trough 110 has a first end 310, a second end 312, and a curved nadir 314. The first end 310 and the second end 312 may be considered as defining a proximal side 350 of the trough or the retractor, with the nadir 314 defining a distal side 360 opposite the proximal side. An exterior side 120 of the trough rests on the exterior of the mouth, while the interior side 130 of the trough rests on the interior of the mouth between the cheek and the teeth (i.e. in the vestibule). A trough face 306 forms the U-shape of the trough and physically contacts the patient.

As seen in FIG. 1, a joint 125 connects the retractor 100 with the arm 40. The joint is located on the exterior side 120 of the trough and on the distal side 360 of the retractor. Here, the joint 125 is depicted as a slot 129 which accepts a tab 44 on the end of the arm 40. The joint 125 extends laterally away from the ends 310, 312 of the trough, or in other words extends laterally from the nadir 314 of the trough 110 away from the ends 310, 312. The trough 110 has a depth 112 of from about 0.25 inches to about 0.5 inches on both the exterior side 120 and the interior side 130. When viewed from the side as in FIG. 4, the trough should be symmetrical, or in other words the depth 112 is the same when measured from either the exterior side 120 or the interior side 130. The retractor 100 is oriented so that the first end 310 and second end 312 are closer to, or proximal to, the center of the arm 40.

A ridge 140 extends transversely from the trough 110. The ridge 140 can be considered as extending in a longitudinal direction away from the arm 40. The ridge can also be considered as being attached to the interior side 130 and the distal side 360 of the trough 110, and extending into the mouth. The ridge 140 extends laterally away from the ends 310, 312 of the trough as well. An angle θ can be defined relative to the plane 142 of the interior side 130 of the trough from which the ridge extends, and can be considered the angle between the U-shaped trough 110 and the ridge 140. In embodiments, the angle θ is from about 40° to about 80°, including about 50° to about 70°, or about 60°. The ridge 140 may have a length 144 of from about 1 inch to about 1.5 inches, including about 1.25 inches. The ridge 140 may be wider at its end 146 than at its base 148 connecting to the trough (see FIG. 4). At least one light-emitting diode 160 (LED) is secured to the ridge 140. If desired, multiple LEDs (i.e. two, three, four, or more) can be secured to the ridge.

As shown in FIG. 1, three LEDs are attached to the ridge. The LEDs lie in a groove 150 formed in the ridge. As seen from the back side in FIG. 4, holes 152 could be present in the groove where adhesive, such as glue, is used to attach the LEDs to the ridge. However, embodiments are also contemplated where the LED(s) is secured, connected, or otherwise attached to the ridge, without the use of adhesive, and not in a groove (as described further herein). The LEDs can be located on the ridge as appropriate.

Figure 8:
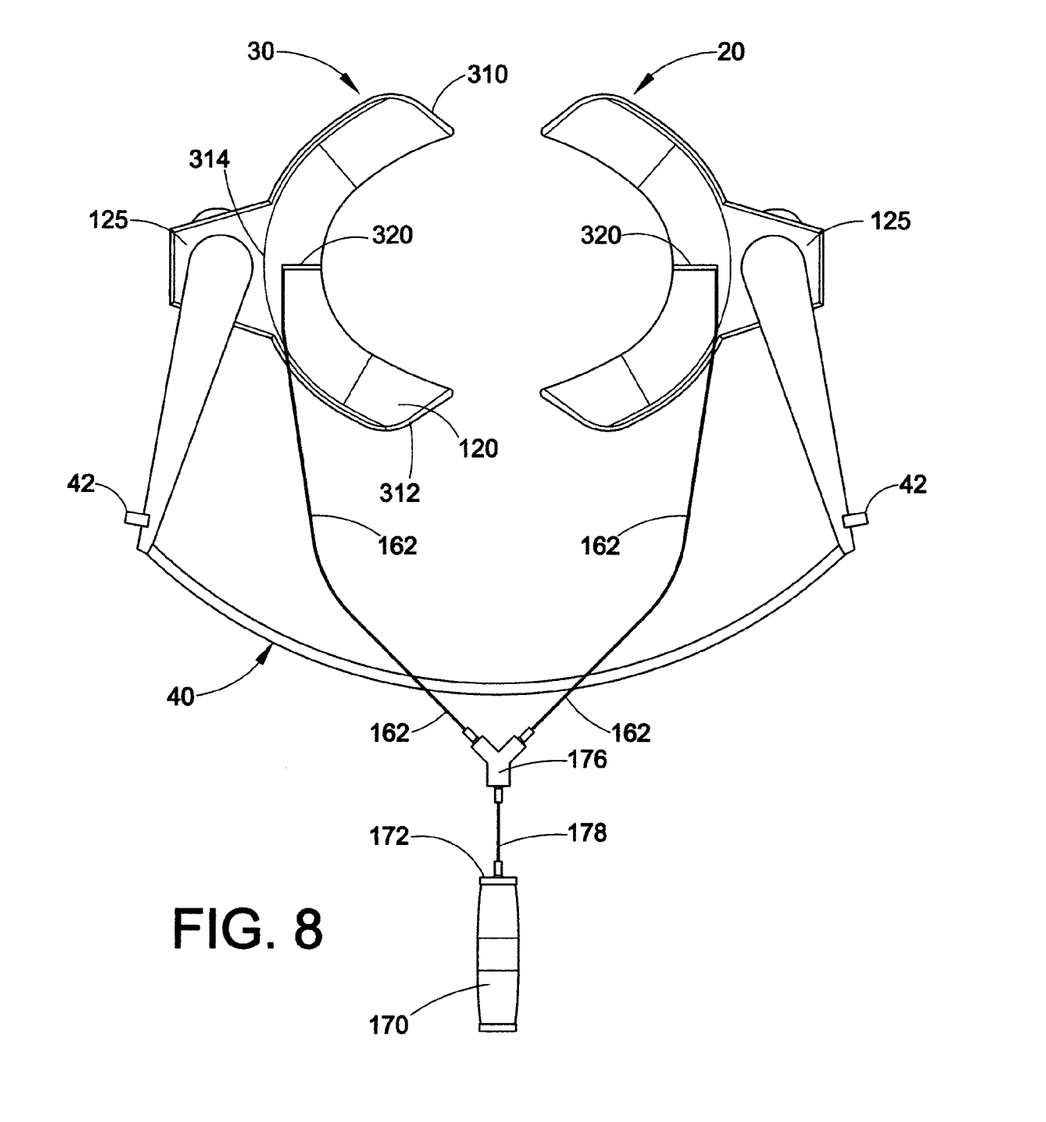
FIG. 8 is a rear view of another exemplary dental apparatus.

A power cord 162 runs from each retractor 20, 30 to an external battery and control system 170 for controlling and powering the LEDs. The external control system 170 has a first end 172 and a second end 174, and also contains a battery or other power source for powering the LEDs. The first end 172 and second end 174 may be on opposite sides of the external control system. As depicted in FIG. 1, the power cord for one retractor 20 is plugged into the first end 172, and the power cord for the other retractor 30 is plugged into the second end 174. The LED(s) on each retractor can then be independently turned on or off, e.g. by separate switches located on this external control system. As depicted in FIG. 8, the power cord for each retractor runs to a "Y" connector 176. A power cord 178 then runs from the Y connector 176 and connects to one end 172 of the external control system 170. Here, the LED(s) on the two retractors are turned on and off together. The power cord 162 for each retractor may have a length of from about 12 inches to about 24 inches, and generally is long enough so that the external control system 170 rests on the patient's chest. Similarly, the power cord 178 for the Y connector may have a length of from about 4 inches to about 12 inches, including about 6 inches.

Although the retractors 20, 30 and arm 40 can be sterilized, it may be desirable that they be disposable as well. In some embodiments, the external battery and control system is separable from the retractors, so that the external system can be reused with new retractors. In such embodiments, it is contemplated that the power cord 162 is an integral part of the retractor, and has a sufficient length to reach the external control system 170. The electrical connections from the LED to the power cord are sealed in the retractor itself due to the wet conditions of the mouth, the routine use of water during dental procedures, and the attending electrical hazard. The power cord 162 would be plugged into the external battery and control system. The retractors can be disposed of after one or several uses, or can be sterilized for reuse.

As seen in FIG. 1 and FIG. 3, the LEDs 160 receive power through a wire 320 or similar conducting device. The wire 320 runs from the LED on the ridge 140 to the exterior side 120 of the retractor. The power cord 162 runs from the exterior side 120 to the external control system 170 to provide power to the LEDs. The wire 320 can be embedded in the retractor or located along the surface thereof. The power cord 162 emerges from the exterior side 120 of the retractor, but the specific location thereof is generally not important.

It should be noted that the angle θ between the trough 110 and the ridge 140 allows the ridge to push the cheek away from the teeth as well, enlarging or increasing the size of the oral cavity and keeping the ridge out of the way of the mouth or any equipment used by the dentist.

Using other terms, the cheek retractor 100 includes a lip-oriented face 200 and an oral cavity-oriented face 210 (See FIG. 2 and FIG. 5). A light-emitting diode is located on the oral cavity-oriented face. The lip-oriented face may be a U-shaped trough. The oral cavity-oriented face may be located on a ridge 140 extending transversely from the lip-oriented face and away from the arm 40. In some embodiments, the angle θ between the lip-oriented face 200 and the oral cavity-oriented face 210 is from about 40° to about 80°. In other embodiments, the angle θ is from about 50° to about 70°. In specific embodiments, the angle θ is about 60°.

As noted in FIG. 4 and FIG. 5, the cheek retractor 100 may have a height 212 of about 2.1 inches and a width 216 of about 2 inches. The ridge 140 may extend from the exterior side 120 into the mouth for a lateral distance 214 of about 2 inches.

Figure 6:
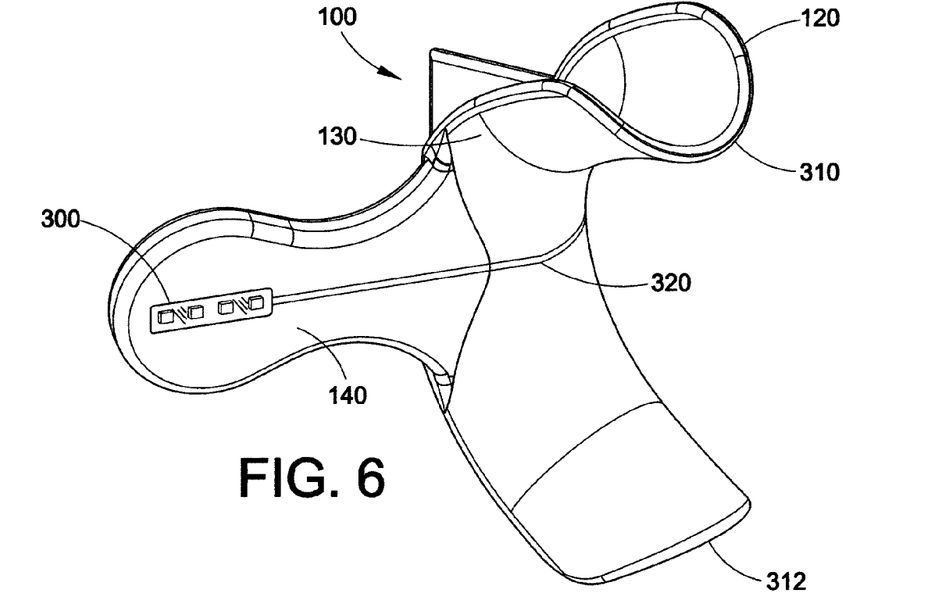
FIG. 6 is a perspective view of a second exemplary dental apparatus.

FIG. 6 depicts another embodiment of a cheek retractor 100 suitable for use in the dental apparatus 10. In this embodiment, there is no groove 150 on the ridge 140. Rather, the LEDs 160 are embedded into the ridge 140. The ridge 140 has a smooth inner surface 300 which is made from a substantially transparent material that allows the LED light to shine through the inner surface 300 and illuminate the oral cavity. In embodiments, the material has a transparency (% T) of at least 90%, as measured by ASTM D1003. Many known materials meet this requirement, such as acrylic, polyester, epoxy, urethane, polycarbonate, and nylon resins.

Figure 7:
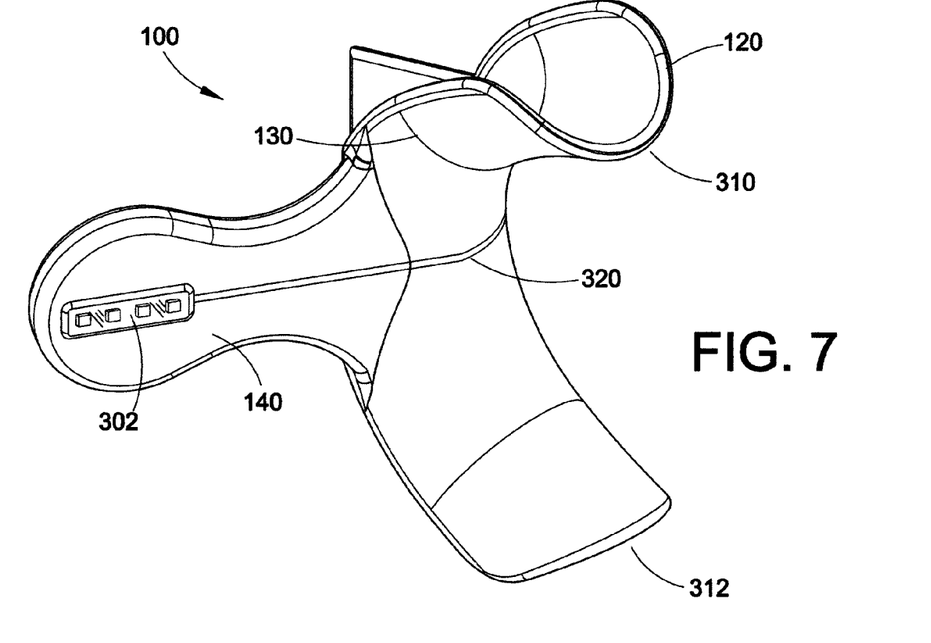
FIG. 7 is a perspective view of a third exemplary dental apparatus.

In other embodiments shown in FIG. 7, the ridge 140 has a raised inner surface 302 instead, with the LEDs 160 still being embedded into the ridge 140. In both FIG. 6 and FIG. 7, the LEDs can be connected to the power cord 162 of FIG. 1. It should be noted that the LEDs 160 are placed along a centerline 304 of the ridge 140.

Stenson's duct opens upon the inner surface of the cheek by a small orifice opposite the first or second molar tooth of the upper jaw. As seen in FIG. 4, the ridge 140 may be offset towards the superior edge 330 of the retractor 100 or the trough 110, and away from the inferior edge 340. Put another way, the ridge is closer to the superior edge 330 than the inferior edge 340. This offset allows the ridge 140 to cover Stenson's duct, reducing the amount of saliva actually introduced into the oral cavity or at least redirecting the saliva along the inner surface of the cheek. The distance between the ridge 140 and the superior edge 330 can be considered the superior height 335, and the distance between the ridge 140 and the inferior edge 330 can be considered the inferior height 345. The superior height 335 can be about 0.3 inches. The inferior height 345 can be about 0.7 inches. In other embodiments, the ratio of the superior height 335 to the inferior height 345 is from about 0.2 to about 0.8, including about 0.4. It should be noted that both retractors 20, 30 have this offset of the ridge towards the upper lip. Thus, the two retractors 20, 30 can be considered mirror images of each other, but they are not interchangeable with each other. Put another way, one retractor 20 is considered a left retractor, while the other retractor 30 is considered a right retractor.

Regarding FIG. 8, it is also contemplated that in some embodiments, the two retractors 20, 30 are integrally connected to each other through the Y connector 176. Put another way, the power cords 162 of the two cheek retractors are joined together to form a Y connection. The external control system 170 then needs only one socket into which the Y connector is plugged. Another advantage of these embodiments is that the combination of the retractors, power cords, and Y connector provide directionality to the assembly and it is clear which retractor should be attached to which end of the flexible arm 40.

The various parts of the dental apparatus can be made by methods known in the art. For example, molds can be made for the desired shapes of the retractors and arms. Molten polymer is poured into the molds and then cooled into solid form to form the retractor. The retractor is removed from the molds and LEDs are attached to the retractors using fasteners or adhesives such as glue. Alternatively, the LEDs are placed in the mold and the resin is poured into the mold to encase or embed the LEDs. As yet another alternative, a mold is made containing a groove. The LEDs are then placed into the groove, and resin is then poured to fill in the groove and encase or embed the LEDs. Generally, the trough 110 and ridge 140 of the retractor are made from the same material for ease of manufacture. The material used to make the retractor should be a biocompatible and/or medical grade polymeric material. Desirably, the material has low or zero water absorption, i.e. does not absorb water.

The apparatuses of the present disclosure have been described with reference to exemplary embodiments. Obviously, modifications and alterations will occur to others upon reading and understanding the preceding detailed description. It is intended that the exemplary embodiments be construed as including all such modifications and alterations insofar as they come within the scope of the appended claims or the equivalents thereof.

The invention claimed is:

1. A dental apparatus for retracting and illuminating the oral cavity of a patient, comprising:
   two cheek retractors; and
   a flexible arm connecting the two retractors;
   wherein at least one of the two cheek retractors comprises:
      a U-shaped trough, the trough having an interior side and an exterior side;
      a ridge extending transversely from the interior side of the trough in a longitudinal direction away from the arm, an inner surface of the ridge having a groove formed within the ridge that extends between a base of the ridge and an end of the ridge along a centerline of the ridge, the base of the ridge connecting to the trough;
      a joint on the exterior side of the trough for connecting the retractor to the arm;
      a plurality of light-emitting diodes (LEDs) embedded in the groove within the ridge in only a single row extending from the base of the ridge to the end of the ridge; and
      a wire running from the plurality of LEDs on the ridge to the exterior side of the trough.

2. The dental apparatus of claim 1, wherein the ridge is wider at the end than at the base.

3. The dental apparatus of claim 1, further comprising a power cord for powering the plurality of LEDs, the power cord extending from an exterior side of the trough.

4. The dental apparatus of claim 1, wherein each U-shaped trough has a depth of from about 0.25 to about 0.5 inches.

5. The dental apparatus of claim 1, wherein the angle between the U-shaped trough and the ridge is from about 50° to about 70°.

6. The dental apparatus of claim 1, wherein the angle between the U-shaped trough and the ridge is about 60°.

7. The dental apparatus of claim 1, wherein the arm includes at least one securing member for holding a hose.

8. The dental apparatus of claim 1, further comprising an external battery and control system for powering the plurality of LEDs on the retractor.

9. The dental apparatus of claim 1, wherein the ridge has a smooth inner surface.

10. The dental apparatus of claim 1, wherein the ridge has a raised inner surface.

11. The dental apparatus of claim 1, wherein the ridge comprises a substantially transparent material through which the plurality of LEDs can transmit light.

12. The dental apparatus of claim 11, wherein the substantially transparent material has a transparency of at least 90 percent as measured by ASTM D1003.

13. A dental apparatus used to enlarge and illuminate the oral cavity of a patient, comprising:
   two cheek retractors; and
   a flexible arm connecting the two retractors;
   wherein at least one of the two cheek retractors comprises:
      a U-shaped trough having an interior side and an exterior side; a joint on the exterior side of the trough for connecting the retractor to the arm;
      an oral cavity-oriented face;
      a plurality of light emitting diodes (LEDs) secured within a groove in the oral cavity-oriented face, wherein the oral cavity-oriented face is on a ridge extending transversely from the interior side of the U-shaped trough in a longitudinal direction away from the arm, the groove extending along a centerline of the ridge, and the LEDs being placed in only a single row from a base of the ridge to an end of the ridge, the base of the ridge connecting to the trough; and
      a wire running from the plurality of LEDs on the ridge to the exterior side of the trough.

14. A dental apparatus for illuminating the oral cavity of a patient, comprising:
   two cheek retractors;
   a flexible arm connecting the two retractors; and
   an external control system; wherein each cheek retractor comprises:
      a U-shaped trough having two ends, a nadir, an interior side, and an exterior side;
      a ridge attached to the interior side of the trough, extending transversely from the trough and including a groove within an inner surface of the ridge that extends between a base of the ridge and an end of the ridge along a centerline of the ridge, the base of the ridge connecting to the trough;
      a plurality of light-emitting diodes (LEDs) secured within the groove in only a single row extending from the base of the ridge to the end of the ridge;
      a joint on the exterior side of the trough for connecting the cheek retractor to the arm, the joint having a slot and extending from the nadir away from the two ends of the trough; and a power cord extending from the exterior side of the trough for powering the plurality of LEDs;
      a wire running from the plurality of LEDs on the ridge to the exterior side of the trough;
      wherein the arm has two ends, each end having a tab that engages the slot on the joint to connect the cheek retractor to the arm;
      wherein the external control system includes a battery for powering the plurality of LEDs on each cheek retractor.

15. The dental apparatus of claim 14, wherein the power cords of the two cheek retractors are joined together to form a Y connection, integrally connecting the two retractors.

16. The dental apparatus of claim 14, wherein the ridge has a smooth inner surface.

17. The dental apparatus of claim 14, wherein the ridge comprises a substantially transparent material through which the plurality of LEDs can transmit light.

* * * * *